US00PP32089P2

(12) United States Plant Patent
Jones et al.

(10) Patent No.: US PP32,089 P2
(45) Date of Patent: Aug. 18, 2020

(54) ***ACHILLEA* PLANT NAMED 'HEARTTHROB'**

(50) Latin Name: *Achillea millefolium*
Varietal Denomination: HEARTTHROB

(71) Applicants: Sidney James Jones, Cwmbran (GB); David James Jones, Caldicot (GB)

(72) Inventors: Sidney James Jones, Cwmbran (GB); David James Jones, Caldicot (GB)

( * ) Notice: Subject to any disclaimer, the term of this patent is extended or adjusted under 35 U.S.C. 154(b) by 0 days.

(21) Appl. No.: 16/501,968

(22) Filed: Jul. 11, 2019

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 6/14; A01H 5/02
See application file for complete search history.

*Primary Examiner* — Keith O. Robinson
(74) *Attorney, Agent, or Firm* — Cochran Freund & Young LLC; James M. Weatherly

(57) ABSTRACT

A new cultivar of *Achillea* plant named 'HEARTTHROB' that is distinguishable by basal branching, upright and spreading plant habit, fern-like foliage which is grey-green in color at time of flowering, inflorescences which consist of bright red ray flowers and yellow disc flowers forming a contrasting eye. Flowering of 'HEARTTHROB' commences in late June and continues until October on plants which are 45 cm in height and 35 cm in width after 1 year of growth from an initial cutting.

2 Drawing Sheets

Genus and species: *Achillea millefolium.*
Variety denomination: 'HEARTTHROB'.

BACKGROUND OF THE NEW PLANT

The present invention relates to a new and distinct cultivar of *Achillea* commonly known as Yarrow, which is grown as an ornamental plant for use in the garden and landscape. The new cultivar is known botanically as *Achillea millefolium* and will be referred to hereinafter by the cultivar name 'HEARTTHROB'.

*Achillea* is a genus within the family Asteraceae in which the commonly referred to "flower" is botanically the inflorescence which is comprised of outer showy ray florets surrounding smaller disc florets. The inflorescences of *Achillea* are borne in clusters or corymbs.

'HEARTTHROB' arose and was selected from an ongoing breeding program which is conducted by the inventor at the inventor's nursery in Penhow, Wales, United Kingdom. The breeding program commenced in 2014 with the aim of developing new and improved commercial varieties of *Achillea*. Each year's breeding cycle consists of controlled pollination between chosen male and female parents including unnamed and unreleased seedlings retained from previous breeding cycles. Seed from each year's cycle is harvested and sown in the fall, and new seedlings are raised and evaluated in the following summer.

'HEARTTHROB' is a seedling selection that resulted from the controlled pollination in 2015 of a single plant of the inventor's proprietary *Achillea* seedling code AC 89 (unreleased and unpatented) as the female parent, using pollen from a single plant of the inventor's proprietary *Achillea* seedling code AC 201 (unreleased and unpatented) as the male parent. The inventor selected 'HEARTTHROB' in 2016 for its combination of large and colorfast bright red blooms with contrasting yellow "eyes" and which are borne on strong stems, and blue-green fern-like foliage.

'HEARTTHROB' was first asexually propagated by the inventor in Penhow, Wales, United Kingdom in 2016 using the method of shoot tip cuttings. Since that time under careful observation 'HEARTTHROB' has been determined uniform, stable and true to type in subsequent generations of asexual propagation.

SUMMARY

The following traits have been repeatedly observed and represent the distinguishing characteristics of 'HEARTTHROB'. In combination these traits set 'HEARTTHROB' apart from all other existing varieties of *Achillea* known to the inventor. 'HEARTTHROB' has not been tested under all possible conditions and phenotypic differences may be observed with variations in environmental, climatic, and cultural conditions, however, without any variance in genotype.

1. 'HEARTTHROB' exhibits tight clumping basal-branching and an upright plant habit.
2. The juvenile foliage of 'HEARTTHROB' is bright mid-green in color, becoming grey-green in color at and after flowering.
3. The foliage of 'HEARTTHROB' is finely dissected and fern-like in appearance.
4. A fully expanded corymb of 'HEARTTHROB' is 5.5 cm to 6.0 cm in diameter and is comprised of inflorescences which contain ray florets arranged around a central disc.
5. The ray florets of 'HEARTTHROB' are arranged in a single horizontal plane.
6. The ray florets of 'HEARTTHROB' are bright red in color.

7. The mass of disc florets of 'HEARTTHROB' are yellow in color, forming an "eye" within each inflorescence.
8. The flowers of 'HEARTTHROB' are carried on strong stiff stems.
9. Flowering of 'HEARTTHROB' commences in mid-late June and continues until October.
10. After one year of growth in a 2 gallon container, or planted in the ground, a plant of 'HEARTTHROB' is 45 cm in height (including the flowers) and 35 cm in width.
11. 'HEARTTHROB' is hardy in USDA Zone 3 (−40° F. or −40° C.).

COMPARISON WITH PARENTAL LINES AND KNOWN VARIETY

In comparison with the female parent, seedling code AC 89, 'HEARTTHROB' is shorter and more compact in size and bears its flowers, which are similarly bright red in color, on shorter stems. In comparison with the male parent, seedling code AC 201, 'HEARTTHROB' bears bright red flowers whereas AC 201 bears red-purple flowers.

The commercial variety of *Achillea* which the inventor considers to most closely resemble 'HEARTTHROB' is *Achillea* Plant Named 'Pomegranate' (U.S. Plant Pat. No. 20,763). In comparison with 'Pomegranate', although the plant habits and sizes are very similar, the ray florets of 'HEARTTHROB' are bright red in color whereas the ray florets of 'Pomegranate' are red-purple in color.

BRIEF DESCRIPTION OF THE PHOTOGRAPHS

The accompanying color photographs illustrate the overall appearance of 'HEARTTHROB' showing the color of foliage and inflorescence as true as is reasonably possible to obtain in color reproductions of this type. The photographs were taken from one-year old plants which were growing in-ground out of doors in Oxnard, Calif., without any pruning or use of chemical growth regulators. The colors in the photographs may differ from color values cited in the detailed botanical description, which accurately describe the colors of 'HEARTTHROB'.

FIG. 2 also illustrates the blue-green color of the foliage of 'HEARTTHROB' at flowering stage.

BOTANICAL DESCRIPTION OF THE PLANT

Figure 1:
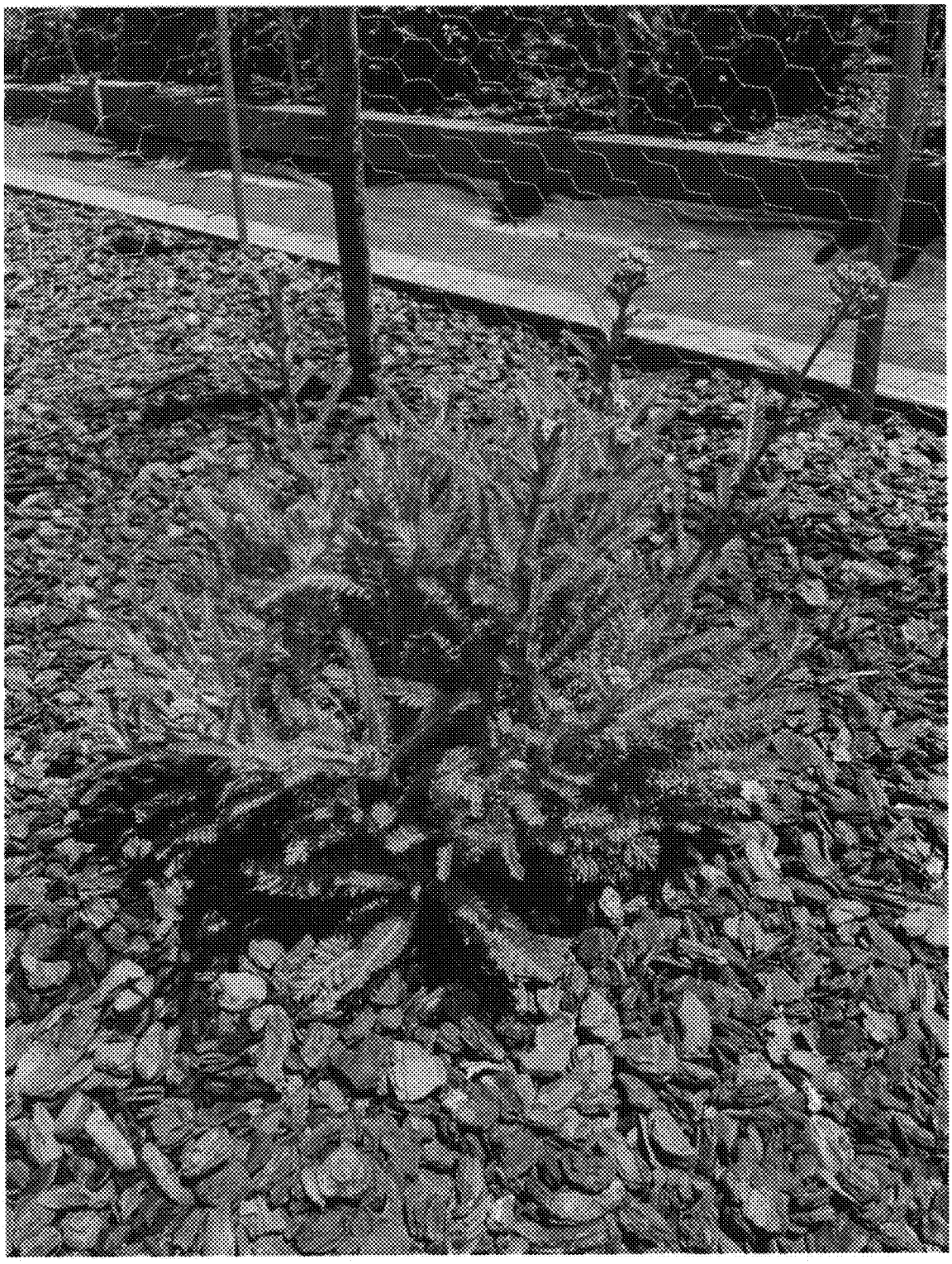
FIG. 1 illustrates a plant of 'HEARTTHROB' which is just coming into bud in early June. At this early stage of flowering, the foliage of 'HEARTTHROB' is bright mid-green in color.
Figure 2:
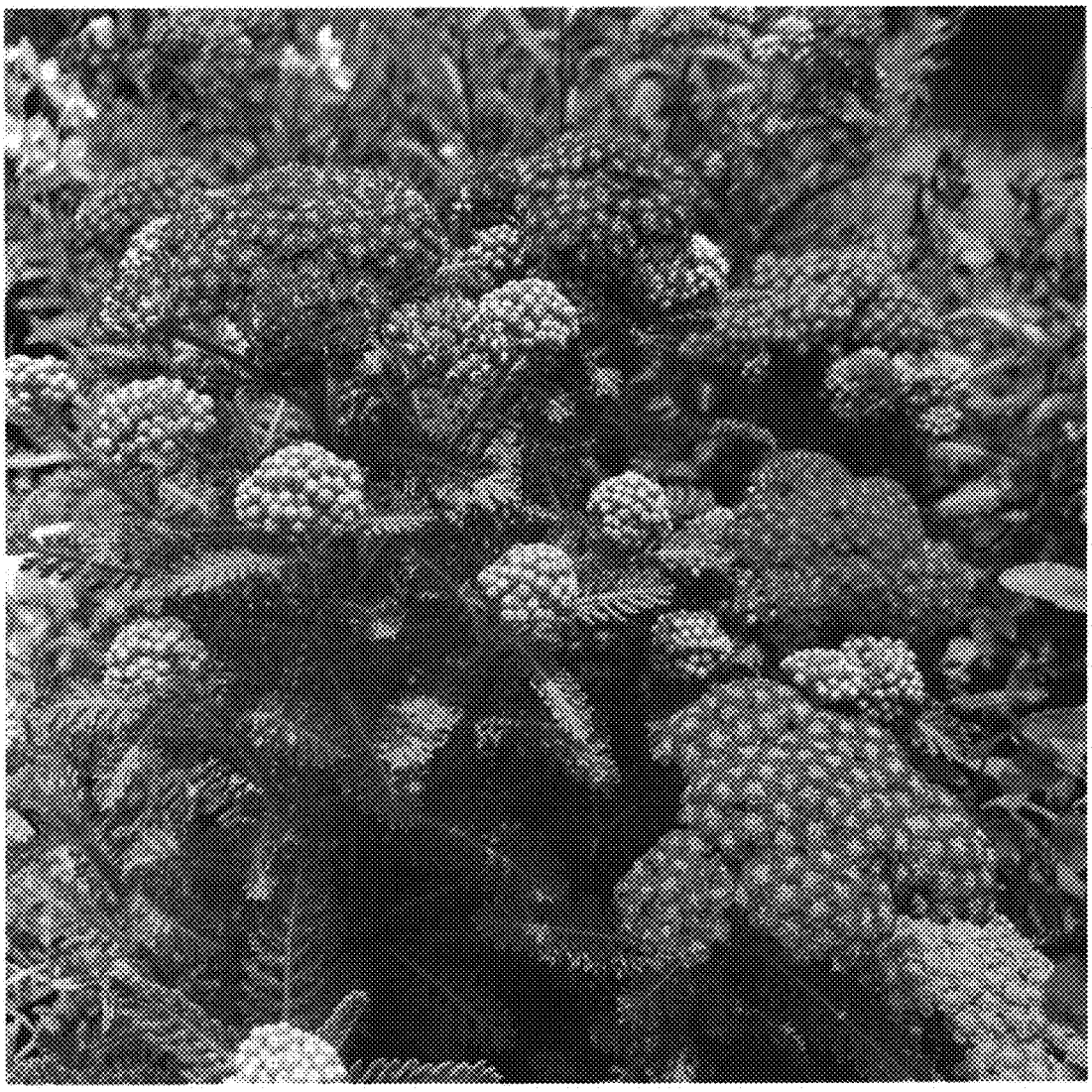
FIG. 2 illustrates the buds and open flowers of the inflorescences of 'HEARTTHROB' in late June.

The following is a detailed botanical description of the new cultivar 'HEARTTHROB'. Observations, measurements, values and comparisons were collected in Oxnard, Calif. during late June 2019 from a 1 year old plant growing in-ground outdoors. Color determinations are made in accordance with The 2007 Royal Horticultural Society Colour Chart from London, England, except where general color terms of ordinary dictionary significance are used.

Botanical classification:

*Family*.—Asteraceae.

*Genus*.—*Achillea*.

*Species*.—*Millefolium*.

*Denomination*.—'HEARTTHROB'.

*Common name*.—Yarrow.

*Habit*.—Basal-branching, upright and spreading.

*Commercial category*.—Perennial.

*Use*.—For garden and landscape.

*Suggested commercial container size*.—4-inch, 1 gallon, 2 gallon containers.

*Parentage*.—*Achillea millefolium* 'HEARTTHROB' is a seedling selection resulting from the controlled cross-pollination of the following parents. Male parent: inventor's proprietary *Achillea* seedling code AC 89. Female parent: inventor's proprietary *Achillea* seedling code AC 201.

*Propagation method*.—Shoot tip cuttings.

*Rooting system*.—Fine and fibrous.

*Time to develop roots* (*range*).—14 to 21 days are needed for an initial cutting to develop roots.

*Temperature to develop roots* (*range*).—The recommended air temperature is 20° C. to 21° C.

*Crop time* (*from planting a rooted cutting*).—6 to 8 weeks to produce a budded plant in a 1-quart container. 12 to 14 weeks to produce a flowering plant in a 1-gallon container.

*Plant dimensions* (*one year*).—45 cm in height (including the flowers) and 35 cm in width.

*Cultural requirements*.—Grow in full sun and rich, moist moderately fertile well-draining soil.

*Pest or disease resistance and susceptibility*.—Deer resistant and salt tolerant. Otherwise, no specific disease or pest resistance or susceptibility has been observed.

*Hardiness*.—USDA Zone 3.

Stem:

*Branching*.—Basal, typically 6 to 8 flowering stems arise from the base.

*Branch and flower stem shape*.—Cylindrical.

*Branch dimensions* (*foliage*).—25 cm to 30 cm in length, 8 mm in diameter at base, narrowing to 3 mm towards apex.

*Flowering stem dimensions*.—25 cm to 40 cm in length (to base of corymb), 8 mm in diameter at base, narrowing to 3 mm at corymb.

*Branch and flowering stem surfaces*.—Ribbed longitudinally.

*Branch and flowering stem color*.—147D, ribs 178B.

Foliage:

*Type* (*division*).—Pinnatifid.

*Arrangement*.—Alternate, spiral, cauline (flower stems).

*Internode length* (*range*).—1.5 cm to 2.0 cm.

*Margin*.—Very finely dissected into approximately 25 pairs of opposite leaflets.

*Apex*.—Acute.

*Base*.—Truncate.

*Leaf attachment*.—Sessile.

*Leaf angle*.—Acute, close to 45 degrees, between adaxial surface and stem.

*Leaf color* (*both surfaces, juvenile foliage prior to flowering*).—141C.

*Leaf color* (*both surfaces, at and after flowering*).—N138B.

*Leaf shape*.—Lanceolate.

*Leaf dimensions*.—5 to 7 cm in length, 18 mm in width at base.

*Leaf venation*.—Pinnate.

*Vein color* (*both surfaces*).—Indistinguishable from leaf color.

*Leaf surface* (*both surfaces*).—Faintly puberulent.

Inflorescence:

*Inflorescence type*.—Indeterminate compound corymb consisting of small single inflorescences comprising ray florets, disc florets, receptacle and phyllaries.

*Corymb quantity per plant*.—25 to 30.

*Corymb shape*.—Flattened dome.

*Corymb dimensions*.—8 to 10 cm in width, 3 to 4 cm in height.

*Corymb peduncles*.—Dimensions (primary peduncles, stem to lowest corymb): 5 cm in length, 1.5 mm in diameter. Dimensions (secondary peduncles, subtending pedicels): 1.0 cm to 2.5 cm in length, 1.0 mm to 1.5 mm in diameter. Shape: Cylindrical. Color: 146D. Surface: Lightly pubescent; hairs fine, white, less than 0.5 mm in length.

*Inflorescence pedicels*.—Dimensions: 2 to 4 cm in length, 1.0 mm to 1.5 mm in diameter. Pedicel color: 146D. Pedicel surface: Lightly pubescent; hairs fine, white, less than 0.5 mm in length.

*Inflorescence quantity per corymb* (*average*).—50 to 80.

*Inflorescence diameter* (*fully opened*).—9 mm.

*Inflorescence depth*.—5 mm.

*Inflorescence aspect*.—Upright.

*Inflorescence colors* (*when fully developed*).—Ray florets: Ranges between 42A and 45C. Disc florets (massed in central disc): 23B.

*Fragrance*.—Musty.

*Blooming season*.—Late June to October.

*Lastingness of inflorescence* (*range*).—10 to 14 days on the plant, persistent.

Bud:

*Shape*.—Ovoid.

*Dimensions*.—3 mm in diameter, 3.5 mm to 4.0 mm in height.

*Color*.—147B.

*Surface*.—Glabrous.

Ray florets:

*Ray floret arrangement*.—Rotate, single whorl.

*Quantity*.—5 per inflorescence.

*Aspect*.—Horizontal.

*Corolla tube dimensions*.—2.5 mm in length, 0.5 mm in diameter.

*Corolla tube color*.—180A.

Ray floret petals:

*Shape*.—Circular except some petals exhibit 3-lobed apices.

*Surface* (*both surfaces*).—Glabrous.

*Apex*.—Round, occasionally emarginate (3-lobed).

*Margin*.—Entire.

*Dimensions*.—4 mm in diameter.

*Color* (*both surfaces*).—Ranges between 42A and 45C.

Disc floret:

*Disc diameter*.—3.0 cm.

*Disc color* (*mass of disc florets*).—23B.

*Disc floret quantity*.—Approximately 20.

*Disc floret shape*.—Tubular.

*Disc floret dimensions*.—6 mm to 7 mm in length (including corolla tube), 1 mm in diameter.

*Disc floret corolla*.—5 lobed, color N155D.

*Disc floret petals*.—5. Dimensions: 5, 2 mm in length, 0.5 mm in width. Color (both surfaces): 23B. Surface (both surfaces): glabrous. Apex: Rounded. Base: Truncate. Margin: Smooth, entire.

Receptacle:

*Shape*.—Slightly convex; diameter 3 cm, height 0.5 cm; color 146D.

Phyllaries:

*Description*.—Appear as paper like bracts or scales which subtend the ray florets and the outermost disc florets.

*Quantity*.—Approximately 15.

*Shape*.—Lanceolate.

*Dimensions*.—2.5 mm in length, 1 mm in width.

*Apex*.—Acute.

*Base*.—Truncate.

*Margins*.—Entire.

*Surface texture* (*both surfaces*).—Glabrous.

*Color* (*both surfaces*).—146C.

Reproductive organs:

*Ray flowers*.—Androecium (stamens, filaments, anthers, pollen): Absent. Gynoecium: Pistil: 1, 3 mm in length, diameter less than 0.5 mm. Stigma: Bifid, 1 mm in length, color 157D. Style: Cylindrical, 1.5 mm in length, less than 0.5 mm in diameter, color 157D. Ovary (observed immature only, barren): Inferior, ovate, length less than 1 mm, diameter less than 0.5 mm, color 157D.

*Disc flowers*.—Androecium: Stamens: 5, fused at base. Filaments: Length 1 mm, diameter less than 0.5 mm, color white. Anthers: Cylindrical, length 0.7 mm, diameter<0.5 mm, color 8C. Pollen: Moderate, color 15A. Gynoecium: Pistil: 1, 2 mm in length, diameter less than 0.5 mm. Stigma: Bifid, 1 mm in length, color 157D. Style: Cylindrical, 1 mm in length, less than 0.5 mm in diameter, color 157D. Ovary (observed immature only): Inferior, ovate, length less than 1 mm, diameter less than 0.5 mm, color 157D.

Seed: None observed to date.

We claim:

1. A new and distinct cultivar of *Achillea* plant named 'HEARTTHROB' as described and illustrated herein.

* * * * *